(12) United States Patent
Kanca, III

(10) Patent No.: US 7,665,992 B2
(45) Date of Patent: Feb. 23, 2010

(54) THREE PART DENTAL BONDING COMPOSITIONS AND METHODS OF USE

(75) Inventor: John A. Kanca, III, 264 Mirey Dam Rd., Middlebury, CT (US) 06762

(73) Assignee: John A. Kanca, III, Middlebury, CT (US)

(*) Notice: Subject to any disclaimer, the term of this patent is extended or adjusted under 35 U.S.C. 154(b) by 0 days.

(21) Appl. No.: 12/272,103

(22) Filed: Nov. 17, 2008

(65) Prior Publication Data

US 2009/0098514 A1 Apr. 16, 2009

Related U.S. Application Data

(62) Division of application No. 11/360,978, filed on Feb. 23, 2006, now Pat. No. 7,452,925.

(60) Provisional application No. 60/656,498, filed on Feb. 25, 2005.

(51) Int. Cl.
*A61C 5/00* (2006.01)

(52) U.S. Cl. ................. 433/228.1; 433/217.1; 523/116; 523/118

(58) Field of Classification Search ............... 433/228.1; 523/116, 118
See application file for complete search history.

(56) References Cited

U.S. PATENT DOCUMENTS

| RE34,937 E | * | 5/1995 | Ibsen et al. ................ 106/35 |
| 5,756,560 A | * | 5/1998 | Antonucci et al. .......... 523/118 |
| 6,071,983 A | * | 6/2000 | Yamamoto et al. .......... 523/118 |
| 6,458,869 B1 | * | 10/2002 | Antonucci et al. .......... 523/118 |
| 7,041,164 B2 | * | 5/2006 | Kanca, III .................... 106/35 |
| 7,226,960 B2 | * | 6/2007 | Jia ............................ 523/115 |

* cited by examiner

*Primary Examiner*—Tae H Yoon
(74) *Attorney, Agent, or Firm*—Scott D. Rothenberger; Fulbright & Jaworski

(57) ABSTRACT

Three part bonding compositions that include an etching solution, a preparative solution, and a curable composition, as well as packaged products and methods of use for the treatment of bone substrate, i.e., teeth, are described. The etch solutions generally include an inorganic acid, an organic acid, an ethylenically unsaturated functional monomer and, optionally a solvent, and water. The preparative solutions generally include an ethylenically unsaturated functional monomer, at least one polyethylenically unsaturated functional crosslinking monomer, a photo initiator, and at least one solvent. The curable composites include reactive monomers and crosslinking agents that are effective to adhere to the surface of the treated substrate. The methods of the invention provide the ability to modify a bone or bone-like surface so that the curable composition, such as an adhesive resin, can be used in combination with a restorative material.

17 Claims, No Drawings

THREE PART DENTAL BONDING COMPOSITIONS AND METHODS OF USE

CROSS REFERENCE TO RELATED APPLICATIONS

This application is a divisional of Ser. No. 11/360,978 filed on Feb. 23, 2006, now U.S. Pat. No. 7,452,925, which priority to of U.S. Provisional Patent Application No. 60/656,498, filed on Feb. 25, 2005, the entire contents of both of which are incorporated herein by reference.

FIELD OF THE INVENTION

The present invention relates to dental etching solutions, reactive monomeric based adhesive compositions, packaged pharmaceuticals that contain the etch solution and adhesive composition and methods for their use. More specifically, the present invention relates to a superior three step, three part process, whereby an etch solution is applied to a tooth and subsequently causes the dentin to become receptive to adhesive compositions. After the reaction has occurred, a second preparative solution is applied followed by an adhesive composition that is applied to the tooth and the tooth is readied for a restorative material.

BACKGROUND OF THE INVENTION

The use of biomaterials as restorative materials, in both the dental and medical fields is growing and the requirements for such materials are often times difficult to achieve. Restorative materials such as amalgam or resin composites are often used to repair dental tissues and bones.

For example, there has been considerable research devoted to the improvement of the adhesion of resins to hard tissues such as dentin or enamel. The adhesives are typically applied to the hard tissue after a pretreatment or etch of the tissue with an acidic solution. Various resin composites are available and generally suffer one or more disadvantages in providing a satisfactory bond between the tissue and the restorative material. Some of adhesive materials are designed to achieve higher bond strengths between tissue layers or the treated tissue and a restorative material, to improve physical properties, or the esthetics of the restored target substrate. Other desired properties of such adhesive composites are directed to their use and include ease in preparation and formulation for use under relatively humid conditions.

Typically an etch solution is utilized to remove the smear layer and demineralize the surface of the dental tissue. The etch solution can alter wettability or chemical reactivity of the pretreated dentin, prior to applying a bonding adhesive agent which is generally a polymerizable monomer. Polymerization of the bonding agent facilitates the bonding agent to adhere to the dentin. The interaction(s) between the bonding agent and the treated substrate is not entirely understood and is believed to be related to chemical, mechanical, interfacial diffusion or a combination of all three physical processes. Polymerization of most bonding adhesives provide an approximately 5-micron thick hybrid layer that is formed of part resin and part dentin. The depth and effectiveness of the penetration of the bonding agent is an important and often critical aspect to the adhesion between the bonding agent and substrate. This hybrid layer is believed to contain little or no apatite and the adhesion to dentin is believed to occur through collagen with the bonding agent.

Even though there has been continued research in the area of etching solutions and bonding agents, the techniques and/or products currently available for pretreating the dental or bone tissue or adhering a restorative material to the bone or dental tissue have limitations. For example, the bonding agents should effectively seal the dentin tubules to prevent postoperative sensitivity and protect the pulp. Additionally, the bonds should last the lifetime of the restorative correction and be durable under a variety of conditions.

Therefore, a need exists for new compositions, solutions and methods that overcome one or more of the disadvantages of currently available products.

BRIEF SUMMARY OF THE INVENTION

The present invention provides a unique unexpectedly simple and easy to use bone, i.e., tooth, etch solution or in an alternative embodiment, a gel etchant, a second preparative solution, and a curable adhesive bonding composition, packaged products containing one or more of the compositions, and methods to use the compositions of the invention. The systems of the present invention can be self-cured or can be treated with light energy to facilitate curing.

The present invention provides distinct advantages over presently known etching/bonding systems. For example, the present etching solution is not required to be rinsed off, removed and/or dried prior to the application of a bonding composition. Most commercially available bonding systems require that the etch solution is rinsed off and the substrate dried prior to the application of the bonding resin. Alternatively, currently available bonding systems include both an etch solution and the bonding resin as a one component application. Often times, the one component application systems do not bond well to the bone substrate because the etch solution interferes with the ability of the bonding resin to adhere to the substrate.

In one embodiment, the present invention provides a three part bonding system capable of adhering a composite material to bone. In one aspect, the bone is a tooth and more specifically, the substrate is dentin, enamel, amalgam, metal, porcelain or plastic.

In one aspect the present invention provide compositions and methods for adhering a material to a dental substrate. This is accomplished by applying to a dental substrate an effective amount of a dental etching solution, where etch solution includes an inorganic acid, present in an amount of from about 1 to about 10 parts by weight; an organic acid, present in amount from about 0.1 to about 10 parts by weight; a solvent present in an amount from about 0 to about 65 parts by weight; an ethylenically unsaturated functional monomer, present in an amount from about 0.1 to about 10 parts by weight and water, present in an amount from about 0 to about 50 parts by weight, all components in an amount to equal a total of 100 parts by weight.

Alternatively, in place of the etch solution, a gel etchant can be used that includes a gelling agent, an inorganic acid, an organic acid, a surfactant, with the remainder being water. The gelling agent is present in an amount of from about 5 parts to about 40 parts by weight. The inorganic acid is present in an amount of from about 1 to about 10 parts by weight. The organic acid is present in amount from about 0.01 to about 20 parts by weight. The surfactant is present in an amount from about 0.01 to about 10 parts by weight and the water is present in an amount to equal a total of 100 parts by weight of all components.

In another aspect, the gel etchant can include a gelling agent, an inorganic acid, an organic acid, a solvent and water. The gelling agent is present in an amount of from about parts to about 40 parts by weight. The inorganic acid is present in an amount of from about 1 to about 10 parts by weight. The organic acid is present in amount from about 0.01 to about 20 parts by weight. The solvent is present in an amount from about 1 to about 50 parts by weight, with the water being present in an amount to equal a total of 100 parts by weight of all components.

In still yet another aspect, the gel etchant can include a gelling agent, an inorganic acid, an organic acid, an ethylenically unsaturated monomer and water. The gelling agent, inorganic acid and the organic acid are present in the parts described above. The ethylenically unsaturated monomer is present in an amount from about 0.1 to about 10 parts by weight, from about 1.0 to about 5 parts by weight, or from about 2 to about 4 parts by weight, e.g., from about 2 to about 7 parts by weight, e.g., 2.5 parts by weight. The water in the gel etch composition is present in an amount to equal a total of 100 parts by weight of all components. Optionally, a solvent can be added to replace all or part of the aqueous component.

In still another aspect, the gel etchant can include a gelling agent, an inorganic acid, an organic acid, an ethylenically unsaturated monomer, a surfactant and water. The gelling agent, inorganic acid, organic acid, ethylenically unsaturated monomer and surfactant are present in the parts described above. The water in the gel etch composition is present in an amount to equal a total of 100 parts by weight of all components. Optionally, a solvent can be added to replace all or part of the aqueous component.

In a particular embodiment, the gel etchant includes a gelling agent present in an amount from about 5% to about 40%, i.e., about 10%, a surfactant present in an amount from about 0.01% to about 5%, i.e., about 0.1% of Zonyl® FSN, an inorganic acid present in an amount from about 2% to about 20%, i.e., 5% aqueous stock nitric acid, an organic acid present in an amount from about 2% to about 20%, i.e., about 2.5%, succinic acid, an ethylenically unsaturated monomer present in an amount from about 2% to about 20%, i.e., about 2.5% methacrylic acid with the remainder of the gel composition comprising water equal to 100 parts by weight.

In a specific embodiment, the gel etchant includes about 5% nitric acid (stock solution), 2.5% methacrylic acid, 2.5% succinic acid, 9% fumed silica (Aerosil® 200), 0.1% Zonyl® FSN and 80.9% water to equal 100 parts by weight.

The treated dental substrate is subsequently treated with a second preparative solution, where the preparative solution includes an ethylenically unsaturated functional monomer, present in an amount of from about 5 to about 25 parts by weight; a polyethylenically unsaturated functional crosslinking monomer, present in an amount of from about 10 to about 40 parts by weight; a solvent present in an amount from about 0 to about 65 parts by weight; and water, present in an amount from about 0 to about 50 parts by weight, all components in an amount to equal a total of 100 parts by weight;

The surface treated with the second preparative solution is then treated with a curable composite. The curable composite includes an ethylenically unsaturated functional monomer, present in an amount of from about 10 to about 30 parts by weight; a polyethylenically unsaturated functional crosslinking monomer, present in an amount of from about 50 to about 90 parts by weight; a solvent present in an amount from about 0 to about 65 parts by weight; and water, present in an amount from about 0 to about 50 parts by weight, all components in an amount to equal a total of 100 parts by weight.

The surface treated with the curable composite is then exposed to a light source that emits an effective amount of energy to cure the composite.

After activation of the curable composition, a suitable material can be placed about the treated area. The material and treated surface will then be adhered to each other via bonding.

Suitable examples of ethylenically unsaturated functional monomer(s) include, for example, hydroxyethylmethacrylate, methacrylic acid, hydroxypropylmethacrylate, and hydroxybutylmethacrylate. Exemplary polyethylenically unsaturated crosslinking monomer(s) include of PMGDM and bis-GMA.

In one particular aspect, the three part dental bonding system, of the invention includes an etch solution or a gel etchant as described herein, a preparative solution and a curable composite. The etch solution includes nitric acid, present in an amount of about 5 parts by weight; succinic acid, present in amount of about 2.5 parts by weight; methacrylic acid, present in an amount of about 2.5 parts by weight and water, present in an amount to equal a total of 100 parts by weight.

The preparative solution includes hydroxymethylacrylate, present in an amount of about 15 parts by weight; PMGDM, present in an amount of about 20 parts by weight; bis-GMA, present in an amount of about 8 parts by weight; ethanol present in an amount of about 30 parts by weight; and acetone, present in an amount of about 26 parts by weight, all components in an amount to equal a total of 100 parts by weight.

Alternatively, the preparative solution includes hydroxymethylacrylate, present in an amount of about 15 parts by weight; PMGDM, present in an amount of about 25 parts by weight; ethanol and acetone, CQ, present in an amount of about 0.5 parts by weight and Darocur, present in an amount of about 1 part by weight, all components in an amount to equal a total of 100 parts by weight.

The curable compositions of the invention generally include a photo initiator system. The photoinitiator system includes a light-sensitive initiator and a polymerization accelerator. A suitable light-sensitive initiator is camphorquinone (CQ) and a suitable polymerization accelerator is ethyl N,N-dimethyl-4-aminobenzoic acid or ethyldimethylaminobenzoic acid (EDMAB).

The curable composite includes hydroxymethylacrylate, present in an amount of about 20 parts by weight; bis-GMA, present in an amount of about 66.5 parts by weight; and PMGDM, present in an amount of about 10 parts by weight; EDMAB, present in an amount of about 3 parts by weight; CQ, present in an amount of about 0.5 parts by weight, all components in an amount to equal a total of 100 parts by weight.

Alternatively, the curable composite includes hydroxymethylacrylate, present in an amount of about 27 parts by weight; bis-GMA, present in an amount of about 61 parts by weight; PMGDM, present in an amount of about 3 parts by weight; PMDM, present in an amount of about 3 parts by weight, TEGDMA, present in an amount of about 5 parts by weight, EDMAB, present in an amount of about 3 parts by weight and CQ, present in an amount of about 0.5 parts by weight, all components in an amount to equal a total of 100 parts by weight.

The present invention further provides packaged formulations of the three part systems and combinations thereof.

The present invention also provides methods to use the solutions of the invention. It should be understood that the etch solutions and preparative solutions of the present invention can be used with those commercially available bonding resins, i.e., curable compositions.

In one embodiment, the etching solution is applied to an appropriate surface, e.g., bone or tooth that can optionally be dried prior to application. The etch solution is left on the surface for an appropriate period of time; from about one (1) second to several minutes. In this embodiment, the etch solution is not removed from the surface prior to treatment with the second preparative solution. That is, the excess etch solution is not blotted or removed from the surface. Alternatively, the excess etch solution is removed such that the treated surface is either completely dry or left moist. In a particular embodiment, the etch solution is agitated against the surface for approximately ten (10) seconds in order to help the etch solution penetrate into the biological matrix.

Optionally, the etching solution that remains on the surface can be briefly dried. Suitable time periods for drying are from less than a second to 30 seconds and can be accomplished, for example, by use of compressed air.

Following treatment of the surface with the etch solution, one or more applications of the second preparative solution can be applied to the etched surface. Generally, the treated surface is dried for a period of time, for example, 10 seconds, with compressed air, i.e., "air thinning". The bonding resin can then be applied to the treated surface. Generally, a syringe dispenser is used to apply the bonding resin. A thin layer is applied to the treated surface, i.e., the entire cavity preparative area. In one embodiment, multiple applications of the bonding resin are coated onto the surface. For example, two, three or more applications to the surface are within the scope of the present invention.

After the bonding resin (curable composition) is applied to the etched surface, the coated layer(s) can be dried with, for example, compressed air (air thinned). Generally, the surface is dried for about 5 seconds or a sufficient period of time to effectuate solvent removal (if present). Alternatively, the coated layer is not further treated prior to exposure to a curing mechanism, such as a laser, UV light apparatus, LED type curing light, or a quartz-tungsten halogen curing mechanism.

It should be understood that where an etch solution is identified as useful in a method of invention that a comparable gel etchant can be substituted and vice versa. Examples are not intended to be limited when only one aspect, i.e., a solution or gel, is described.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the drawings and detailed description are to be regarded as illustrative in nature and not restrictive.

DETAILED DESCRIPTION

The present invention provides a unique unexpectedly simple and easy to use three-part composition useful for treatment of a substrate, such as bone, i.e., tooth. The three part system includes an etch solution or a gel etchant, a preparative solution, and a curable adhesive bonding composition. The present invention also provides packaged products containing one or more of the components, and methods to use the compositions of the invention. The present invention provides distinct advantages over presently known etching/bonding systems as described throughout the specification.

In one embodiment, the present invention provides a three part dental bonding system that includes an etch solution or gel etchant, a preparative solution and a curable composite. The etch solution includes an inorganic acid, present in an amount of from about 1 to about 10 parts by weight; an organic acid, present in amount from about 0.1 to about 10 parts by weight; a solvent present in an amount from about 0 to about 65 parts by weight; an ethylenically unsaturated functional monomer, present in an amount from about 0.1 to about 10 parts by weight and water, present in an amount from about 0 to about 50 parts by weight, all components in an amount to equal a total of 100 parts by weight.

The preparative solution includes an ethylenically unsaturated functional monomer, present in an amount of from about 5 to about 25 parts by weight; a polyethylenically unsaturated functional crosslinking monomer, present in an amount of from about 10 to about 40 parts by weight; a solvent present in an amount from about 0 to about 65 parts by weight; and water, present in an amount from about 0 to about 50 parts by weight, all components in an amount to equal a total of 100 parts by weight.

The curable composite includes an ethylenically unsaturated functional monomer, present in an amount of from about 10 to about 30 parts by weight; a polyethylenically unsaturated functional crosslinking monomer, present in an amount of from about 50 to about 90 parts by weight; a solvent present in an amount from about 0 to about 15 parts by weight; and water, present in an amount from about 0 to about 15 parts by weight, all components in an amount to equal a total of 100 parts by weight.

In another embodiment, the present invention provides a three part dental bonding system that also includes an etch solution or gel etchant, a preparative solution and a curable composite. The etch solution includes nitric acid, present in an amount of from about 1 to about 10 parts by weight; succinic acid, present in amount from about 0.1 to about 10 parts by weight; methacrylic acid, present in an amount from about 0.1 to about 10 parts by weight and water, present in an amount to equal a total of 100 parts by weight.

The preparative solution includes hydroxymethylacrylate, present in an amount of from about 5 to about 25 parts by weight; PMGDM, present in an amount of from about 15 to about 25 parts by weight; bis-GMA, present in an amount of from about 5 to about 12 parts by weight; ethanol present in an amount from about 25 to about 35 parts by weight; and acetone, present in an amount from about 20 to about 30 parts by weight, all components in an amount to equal a total of 100 parts by weight.

The curable composite includes hydroxymethylacrylate, present in an amount of from about 15 to about 25 parts by weight; bis-GMA, present in an amount of from about 60 to about 70 parts by weight; and PMGDM, present in an amount of from about 5 to about 15 parts by weight, all components in an amount to equal a total of 100 parts by weight.

In still another embodiment, the present invention provides yet a third three part dental bonding system that includes an etch solution or gel etchant, a preparative solution and a curable composite. The etch solution includes nitric acid, present in an amount of about 5 parts by weight; succinic acid, present in amount of about 2.5 parts by weight; methacrylic acid, present in an amount of about 2.5 parts by weight and water, present in an amount to equal a total of 100 parts by weight.

The preparative solution includes hydroxymethylacrylate, present in an amount of about 15 parts by weight; PMGDM, present in an amount of about 20 parts by weight; bis-GMA, present in an amount of about 8 parts by weight; ethanol present in an amount of about 30 parts by weight; and acetone, present in an amount of about 26 parts by weight, all components in an amount to equal a total of 100 parts by weight.

The curable composite includes hydroxymethylacrylate, present in an amount of about 20 parts by weight; bis-GMA, present in an amount of about 66.5 parts by weight; and PMGDM, present in an amount of about 10 parts by weight; EDMAB, present in an amount of about 3 parts by weight; CQ, present in an amount of about 0.5 parts by weight, all components in an amount to equal a total of 100 parts by weight.

It should be understood that throughout the specification, the etching solution or gel etchant can be utilized on any bone or bone-like substrate that includes, but is not limited to, apatite and hydroxyapatite. Bone is a complex mineralizing system composed of an inorganic or mineral phase, an organic matrix phase, and water. The inorganic mineral phase is composed mainly of crystalline calcium phosphate salts while the organic matrix phase consists mostly of collagen and other noncollagenous proteins.

The phrases "etching solution" or "etch solution" are recognized in the art and are intended to include the compositions of the invention that superficially dissolve or modify bone or bone-like substrates. For example, in the case of teeth, the etch solution removes the smear layer and facilitates demineralization of the surface of the dental tissue.

The phrases "gel etching solution", "gel etch solution", "gel etching composition", "gel etchant" and "gel etch composition" are intended to include the compositions of the invention that are gels that superficially dissolve or modify bone or bone-like substrates. For example, in the case of teeth, the gel etch composition removes the smear layer and facilitates demineralization of the surface of the dental tissue.

The gel etchants that can be substituted throughout the specification for the etch solution include those that have a gelling agent and the components described herein.

Suitable gel etchants that can be used include a gelling agent, an inorganic acid, an organic acid, a surfactant, with the remainder being water. The gelling agent is present in an amount of from about 5 parts to about 40 parts by weight. The inorganic acid is present in an amount of from about 1 to about 10 parts by weight. The organic acid is present in amount from about 0.01 to about 20 parts by weight. The surfactant is present in an amount from about 0.01 to about 10 parts by weight and the water is present in an amount to equal a total of 100 parts by weight of all components.

In another aspect, the gel etchant can include a gelling agent, an inorganic acid, an organic acid, a solvent and water. The gelling agent is present in an amount of from about parts to about 40 parts by weight. The inorganic acid is present in an amount of from about 1 to about 10 parts by weight. The organic acid is present in amount from about 0.01 to about 20 parts by weight. The solvent is present in an amount from about 1 to about 50 parts by weight, with the water being present in an amount to equal a total of 100 parts by weight of all components.

In still yet another aspect, the gel etchant can include a gelling agent, an inorganic acid, an organic acid, an ethylenically unsaturated monomer and water. The gelling agent, inorganic acid and the organic acid are present in the parts described above. The ethylenically unsaturated monomer is present in an amount from about 0.1 to about 10 parts by weight, from about 1.0 to about 5 parts by weight, or from about 2 to about 4 parts by weight, e.g., from about 2 to about 7 parts by weight, e.g., 2.5 parts by weight. The water in the gel etch composition is present in an amount to equal a total of 100 parts by weight of all components. Optionally, a solvent can be added to replace all or part of the aqueous component.

In still another aspect, the gel etchant can include a gelling agent, an inorganic acid, an organic acid, an ethylenically unsaturated monomer, a surfactant and water. The gelling agent, inorganic acid, organic acid, ethylenically unsaturated monomer and surfactant are present in the parts described above. The water in the gel etch composition is present in an amount to equal a total of 100 parts by weight of all components. Optionally, a solvent can be added to replace all or part of the aqueous component.

In a particular embodiment, the gel etchant includes a gelling agent present in an amount from about 5% to about 40%, i.e., about 10%, a surfactant present in an amount from about 0.01% to about 5%, i.e., about 0.1% of Zonyl® FSN, an inorganic acid present in an amount from about 2% to about 20%, i.e., 5% aqueous stock nitric acid, an organic acid present in an amount from about 2% to about 20%, i.e., about 2.5%, succinic acid, an ethylenically unsaturated monomer present in an amount from about 2% to about 20%, i.e., about 2.5% methacrylic acid with the remainder of the gel composition comprising water equal to 100 parts by weight.

In a specific embodiment, the gel etchant includes about 5% nitric acid (stock solution), 2.5% methacrylic acid, 2.5% succinic acid, 9% fumed silica (Aerosil® 200), 0.1% Zonyl® FSN and 80.9% water to equal 100 parts by weight.

The terms "comprises" and "comprising" are open ended and are not restrictive in their scope. These terms also include the more restrictive connotations of consisting of and consisting essentially of.

As described above, the etch solutions and/or gel etchants of the present invention include several components. The etch solution or gel etchant can include an inorganic acid, an organic acid, optionally, a solvent, an ethylenically unsaturated functional monomer, a gelling agent and water, all components in an amount to equal a total of 100 parts by weight.

Suitable inorganic acids include nitric acid, sulfuric acid, hydrochloric acid, phosphoric acid and mixtures thereof. In one aspect, the inorganic acid is nitric acid. Nitric acid is generally available as a 70 percent aqueous solution and is utilized at this concentration throughout this application. Sulfuric acid, hydrochloric acid and phosphoric acid are also available as 95-98 percent, 37 percent and 85 percent aqueous solutions, respectively, and are utilized at these concentrations throughout the application. Where noted as parts by weight, this refers to using the concentrated inorganic acid, at the respective commercial concentration, on a weight basis.

Suitable ranges for the inorganic acid component of the etch solution include from about 1 to about 10 parts, from about 3 to about 7 parts, and from about 4 to about 6 parts, all by weight. In a particular embodiment, the inorganic acid is nitric acid.

It should be understood that all values, including non-whole values (integers), inclusive, within the ranges of all concentrations (parts by weight) provided throughout this specification are considered individually. That is, it is within the discretion of the operator to choose any percentage within the ranges provided for any of the metal salts as described herein. Therefore, the ranges provided are not limiting in terms of more narrow ranges and individual values that are encompassed by the parameters of the ranges identified.

It should be noted that commercially available etch solutions that contain phosphoric acid do not work well in dental applications if the solution is not first rinsed from the substrate to which it is applied. This is due to the precipitation of calcium phosphate from the etch solution that is generated by the reaction of phosphoric acid with the calcium of the bone substrate. The present invention avoids such precipitation by either utilizing a different inorganic acid or by using an organic solvent, surfactant and/or organic acid, which inhibit the deposition of calcium phosphate onto the cleaned bone substrate surface.

Suitable organic acids include lactic acid, pyruvic acid, glycolic acid, chloroacetic acid, dichloroacetic acid, trichloroacetic acid, cyanoacetic acid, tartaric acid, succinic acid, glutaric acid, maleic acid, fumaric acid, malonic acid, citraconic acid, ortho-phthalic acid, meta-phthalic acid, para-phthalic acid, citric acid, tricarballyic acid, 1,3,5-pentanetricarboxylic acid and trimellitic acid and mixtures thereof. Other suitable organic acids include 2-acrylamido-2-methylpropane sulfonic acid, benzenesulfonic acid, benzoic acid, bromoacetic acid, 10-camphorquinonesulfonic acid, 10-camphorsulfonic acid, dibromoacetic acid, 2,4-dinitrophenol, formic acid, fumaric acid, 2-hydroxy-4-methoxybenzophenone-5-sulfonic acid, maleic-acid, 2-naphthalene sulfonic acid, nitric acid, oxalic acid, p-nitrophenol, phenol, phosphorous acid esters (such as 2,2'-bis(a-methacryloxy-b-hydroxypropoxyphenyl)propane diphosphonate (Bis-GMA diphosphonate), dibutyl phosphite, di-2-ethyl-hexyl phosphate, di-2-ethylhexyl phosphite, hydroxyethyl methacrylate monophosphate, glyceryl dimethacrylate phosphate, glyceryl-2-phosphate, glycerylphosphoric acid, methacryloxyethyl phosphate, pentaerythritol triacrylate monophosphate, pentaerythritol trimethacrylate monophosphate, dipentaerythritol pentaacrylate monophosphate, and dipentaerythritol pentamethacrylate monophosphate), toluene sulfonic acid, tribromoacetic acid, trifluoroacetic acid, trifluoromethanesulfonic acid, and trihydroxybenzoic acid. Mixtures of such acids can be used if desired. In one aspect, the organic acid is succinic acid or citric acid.

Suitable ranges for the organic acid component of the etch solution include from about 0.1 to about 10 parts, from about 1 to about 5 parts, and from about 2 to about 3 parts, all by weight.

In one aspect, a surfactant can be added to the etch solution, the preparative solution and/or the curable composite. The term "surfactant" is recognized in the relevant art to include those compounds, which modify the nature of surfaces, e.g. reducing the surface tension of water. Surfactants are generally classified into four types: cationic (e.g. modified onium salts, where part of the molecule is hydrophilic and the other consists of straight or branches long hydrocarbon chains such as hexadecyltrimethyl bromide), anionic, also known as amphiphatic agents (e.g., alkyl or aryl or alkylarylsulfonates, carboxylates, phosphates), nonionic (e.g., polyethylene oxides, alcohols) and ampholytic or amphoteric (e.g. dodecyl-beta-alanine, such that the surfactant contains a zwitterionic group). One or more surfactants can be used in the present invention.

Cationic surfactants useful as surface tension reducing agents in the present invention include long chain hydrocarbons, which contain quaternarized heteroatoms, such as nitrogen. Suitable cationic surfactants include quaternary, ammonium compounds in which typically one of the groups linked to the nitrogen atom is a C12-C18 alkyl group and the other three groups are short-chained alkyl groups.

Anionic surfactants (amphiphatic agents) are characterized by a single lipophilic chain and a polar head group, which can include sulfate, sulfonate, phosphate, phosphonate and carboxylate. Exemplary compounds include linear sodium alkyl benzene sulfonate (LAS), linear alkyl sulfates and phosphates, such as sodium lauryl sulfate (SLS) and linear alkyl ethoxy sulfates. Additional examples of anionic surfactants include substituted ammonium (e.g., mono-, di-, and tri-ethanolammonium), alkali metal and alkaline earth metal salts of C6-C20 fatty acids and rosin acids, linear and branched alkyl benzene sulfonates, alkyl ether sulfates, alkane sulfonates, olefin sulfonates, hydroxyalkane sulfonates, fatty acid monoglyceride sulfates, alkyl glyceryl ether sulfates, acyl sarcosinates. acyl N-methyltaurides, and alkylaryl sulfonated surfactants, such as alkylbenzene sulfonates.

Nonionic surfactants do not dissociate but commonly derive their hydrophilic portion from polyhydroxy or polyalkyloxy structures. Suitable examples of polyhydroxy (polyhydric) compounds include ethylene glycol, butylene glycol, 1,3-butylene glycol, propylene glycol, glycerine, 2-methyl-1,3-propane diol, glycerol, mannitol, corn syrup, beta-cyclodextrin, and amylodextrin. Suitable examples of polyalkyloxy compounds include diethylene glycol, dipropylene glycol, polyethylene glycols, polypropylene glycols and glycol derivatives.

Other suitable nonionic surfactants include other linear ethoxylated alcohols with an average length of 6 to 16 carbon atoms and averaging about 2 to 20 moles of ethylene oxide per mole of alcohol; linear and branched, primary and secondary ethoxylated, propoxylated alcohols with an average length of about 6 to 16 carbon atoms and averaging 0-10 moles of ethylene oxide and about 1 to 10 moles of propylene oxide per mole of alcohol; linear and branched alkylphenoxy (polyethoxy) alcohols, otherwise known as ethoxylated alkylphenols, with an average chain length of 8 to 16 carbon atoms and averaging 1.5 to 30 moles of ethylene oxide per mole of alcohol; and mixtures thereof.

Additionally, suitable nonionic surfactants include polyoxyethylene carboxylic acid esters, fatty acid glycerol esters, fatty acid and ethoxylated fatty acid alkanolamides. Block copolymers of propylene oxide and ethylene oxide, and block polymers of propylene oxide and ethylene oxide with propoxylated ethylene diamine are also included as acceptable nonionic surfactants. Semi-polar nonionic surfactants like amine oxides, phosphine oxides, sulfoxides, and their ethoxylated derivatives are included within the scope of the invention.

Suitable amphoteric and zwitterionic surfactants which contain an anionic water-solubilizing group, a cationic group and a hydrophobic organic group include amino carboxylic acids and their salts, amino dicarboxylic acids and their salts, alkylbetaines, alkyl aminopropylbetaines, sulfobetaines, alkyl imidazolinium derivatives, certain quaternary ammonium compounds, certain quaternary phosphonium compounds and certain tertiary sulfonium compounds Examples of anionic, nonionic, cationic and amphoteric surfactants that are suitable for use in the present invention are described in Kirk-Othmer, Encyclopedia of Chemical Technology, Third Edition, Volume 22, pages 347-387, and McCutcheon's Detergents and Emulsifiers, North American Edition, 1983, both of which are incorporated herein by reference.

Typical concentration ranges of surfactant that are useful in the present etch solutions are from about 0.01 parts by weight to about 10 parts by weight, from about 0.1 parts by weight to about 5 parts by weight, and from about 0.5 parts by weight to about 2.5 parts by weight.

The terms "solvent" or "organic solvent" are recognized in the art and are intended to mean those components, other than water, that can be added to the etch solutions of the invention to help solubilize the components and aid in the evaporation of the etch solution from the substrate surface after application. Suitable solvents include those, which are known to be pharmacologically acceptable for treatment of bone tissue. These solvents include dimethyl sulfoxide, ethyl acetate, alcohols and ethers such as methanol, ethanol, propanol, butanol, ethylene glycol, propanediol, butanediol, pentanediol, butenediol, glycerin, trimethylolpropane, hexanetriol, allyl alcohol, diethylene glycol, diethylene glycol monomethyl ether, diethylene glycol monoethyl ether, triethylene glycol, triethylene glycol monomethyl ether, tetraethylene glycol, propylene glycol, dipropylene glycol, tripropylene glycol, 2-methoxyethanol, 2-ethoxyethanol, 2-(methoxyethoxy) ethanol, 2-isopropoxyethanol, 2-butoxyethanol, 1-methoxy-2-propanol, 1-ethoxy-2-propanol, dipropylene glycol, dipropylene glycol monomethyl ether, tripropylene glycol monomethyl ether, glycerine ether and the like, as well as ketones such as acetone, methyl ethyl ketone and the like and mixtures thereof.

Suitable ranges for the solvent component of the etch solution include from about 0 to about 65 parts, from about 1 to about 5 parts, and from about 2 to about 3 parts, all by weight. In a particular embodiment, the etch solution contains no solvent; it is an aqueous solution.

The etch solutions or gel etchants of the present invention can also further include one or more ethylenically unsaturated functional monomers as detailed below.

The phrase "ethylenically unsaturated monomer" includes those reactive agents that include a double bond that can undergo polymerization with other monomers to form a polymeric matrix. The polymerization can be between like monomers or mixtures of monomers. Additionally, the monomers that are ethylenically unsaturated can further react with polyethylenically unsaturated functional crosslinking monomers to form crosslinked networks.

Suitable ethylenically unsaturated monomers, include, but are not limited to ethylene glycol acrylate phosphate (and methacrylate), 2-hydroxyethylacrylate (HEA), 2-hydroxyethylmethacrylate (HEMA), 2- and 3-hydroxypropylacrylate and methacrylate, 1,3 and 2,3-dihydroxypropylacrylate and methacrylate, acrylic acid, methacrylic acid, 2-trimethylammonium ethylmethacrylic chloride, 2-acrylamido-2-methylpropane-sulfonic acid, acrylamide, methacrylamide, 2-hydroxyethylacrylamide and methacrylamide, N,N-bis(2-hydroxyethyl)acrylamide and methacrylamide, N-alkyl-N-hydroxyethyl acrylamides and methacrylamides, 2- and 3-hydroxypropylacrylamide and methacrylamide, methacrylamidopropyltrimethylammonium chloride, gylcerol monomethacrylate and monoacrylate, various reactive ethylenically unsaturated phosphates, and mixtures thereof. It is considered that where an acrylate monomer is suitable the methacrylate analog will likewise be suitable.

Suitable ranges for the ethylenically unsaturated functional monomer component of the etch solution include from about 0.1 to about 10 parts, from about 1 to about 5 parts, and from about 2 to about 3 parts, all by weight. In a particular embodiment, the ethylenically unsaturated functional monomer component of the etch solution is methacrylic acid.

As described above, the gel etch compositions of the present invention include several components. Gelling agents are also known as "thickening agents", and are recognized in the art. Suitable gelling agents for use in the compositions of the invention include those that are known in the art including polyvinylpyrrolidone, carboxypolymethylenes, Pemulen®, Pluronics®, cellulosic ethers, polysaccharide gums, proteins, starches, alignates and fumed silica, i.e., Aerosil® (Degussa).

Polyvinylpyrrolidone, a polymerized polymer of pyrrolidone, is also referred to as "povidone". Polyvinylpyrrolidone is a tertiary amide based polymer. It contains no organic acid in its structure and therefore cannot acid etch or chelate teeth. Polyvinylpyrrolidone is easily dispersed into water to make highly viscous gels for etching at around 5-40% by weight. Polyvinylpyrrolidone may also be considered a tackifying or thickening agent because the increased viscosity of etch composition that it produces has a sticky or tacky feel enabling it to adhere to teeth for the time required to carry out the etching process.

Carboxypolymethylene is a well-known thickening agent that is a slightly acidic vinyl polymer with active carboxyl groups. Suitable carboxypolymethylene compositions may be obtained from B.F. Goodrich Co. under the trade name (CARBOPOL®) as a modified polyacrylic acid hydrophilic polymer, capable of forming viscous gels at concentrations above as little as 5% by weight. These are also referred to as "carbomers".

PEMULEN® is a product of B.F. Goodrich and is used to identify high molecular weight, cross-linked copolymers of acrylic acid and a hydrophobic comonomer. The exact composition of PEMULEN® is unknown since it is a proprietary formulation of B.F. Goodrich.

The term PLURONIC® describes a range of polymers available from BASF, which are also known as poloxamers. The term "poloxamer" is the name for polyoxyethylene polyoxypropylene block copolymers. An example includes POLOXOMER 407, also known as PLURONIC F127.

Alignates include sodium alginate, e.g., Keltone HV, and generally require a cross-linking agent, e.g., a calcium salt, and a sequestrant in order to properly gel. However, when an alkylene glycol alginate is used, neither a calcium salt nor a sequestrant is required in order to gel. The alkylene group may contain from 2 to about 6 carbon atoms. The alkylene glycol alginate should be non-toxic. Preferred is from about 1 to about 15 percent of proylene glycol alginate, which is commercially available as Kelcoloid HVF. When using Kelcoloid HVF, it is preferred to hydrate it first and then add the acid etching solution. The gelling agent is stable in the low pH environment caused by the acid etching composition.

Fumed silica, such as the product offered by Degussa known as AEROSIL®, is an exceptionally pure form of silicon dioxide made by reacting silicon tetrachloride in an oxyhydrogen flame. Particles range from 0.007 to 0.05 µm and tend to link together by a combination of fusion and hydrogen bonding to form chain-like aggregates with high surface areas.

As described above, the second preparative solution includes an ethylenically unsaturated functional monomer, a polyethylenically unsaturated functional crosslinking monomer, a solvent and, optionally, water, all components in an amount to equal a total of 100 parts by weight.

Suitable ethylenically unsaturated functional monomer components of the preparative solution include those described above. Suitable ranges for the ethylenically unsaturated functional monomer component of the preparative solution include from about 5 to about 25 parts, from about 10 to about 20 parts, and from about 12 to about 18 parts, all by weight. In a particular embodiment, the ethylenically unsaturated functional monomer component of the preparative solution is 2-hydroxyethylmethacrylate at a concentration of about 15 parts by weight.

The phrase "polyethylenically unsaturated functional crosslinking monomer" is recognized in the art and is intended to include those crosslinking agents that have two or more reactive double bonds present within the monomeric backbone. The degree of unsaturation provides the ability to polymerize with other crosslinking agent(s) as well as ethylenically unsaturated monomers to form a network of polymerized material.

Suitable crosslinking monomers include, for example, 2-hydroxypropyl-1,3-diacrylate and dimethacrylate, 3-hydroxypropyl-1,2-diacrylate and dimethylacrylate, pentaerythritol diacrylate and dimethacrylate, triethylene glycol dimethacrylate (TEGDMA) and diacrylate, polyethyleneglycol (400) diacrylate and dimethacrylate, glycerol dimethacrylate and diacrylate and pentaerylthritol trimethacrylate and triacrylate, the reaction product of pyromellitic dianhydride with glycerol dimethacrylate (PMGDM), addition product of 2-hydroxyethyl (meth)acrylate and pyromellitic dianhydride (PMDM), pyromellitic dianhydride hemi-mellitic acid, 2,2'-bis[4-(3-methacryloxy-2-hydroxy propoxy)-phenyl]-propane (bis-GMA) and mixtures thereof.

Suitable ranges for the polyethylenically unsaturated functional crosslinking monomer of the preparative solution include from about 10 to about 40 parts, from about 15 to about 30 parts, and from about 20 to about 25 parts, all by weight.

In certain aspects of the invention the polyethylenically unsaturated functional crosslinking monomer of the preparative solution is a combination of two or more crosslinking monomers. For example, in one embodiment, PMGDM and bis-GMA are used in combination. When two or more crosslinking monomers are used in combination, suitable ranges for each component vary to equal the total parts as described above. More specifically, suitable ranges for a first crosslinking agent include from about 5 to about 25 parts, from about 10 to about 22 parts and from about 20 to about 21 parts and suitable ranges for a second crosslinking agent include from about 5 to about 15 parts, from about 8 to about 12 parts and from about 10 to about 15 parts, all by weight. In a particular aspect, the PMGDM of the preparative solution is present at a concentration of about 20 parts by weight and the bis-GMA of the preparative solution is present at a concentration of about 8 parts by weight.

Suitable solvents for the solvent component of the preparative solution include those described above. Suitable ranges for the solvent component of the preparative solution include from about 0 to about 65 parts, from about 20 to about 40 parts, and from about 30 to about 35 parts, all by weight. In a particular embodiment, the preparative solution contains is non-aqueous; it contains less than 2 parts by weight of water.

In certain aspects of the invention the solvent of the preparative solution is a combination of two or more solvents. For example, in one embodiment, ethanol and acetone are used in combination. When two or more solvents are used in combination, suitable ranges for each component vary to equal the total parts as described above. More specifically, suitable ranges for a first solvent include from about 25 to about 35 parts, from about 27 to about 32 parts and from about 29 to about 31 parts and suitable ranges for a second crosslinking agent include from about 20 to about 30 parts, from about 23 to about 29 parts and from about 25 to about 27 parts, all by weight. In a particular aspect, the first solvent of the preparative solution is ethanol, i.e., about 30 parts by weight and the second solvent of the preparative solution is acetone, i.e., about 26 parts by weight.

The preparative solution can further include one or more photo initiators. Suitable photo initiators include benzil 2,3-butanedione, phenyl-1,2-propandione, and camphorquinone (CQ). Suitable ranges of a photo initiator for the preparative solution include from about 0.1 to about 1 part, from about 0.2 to about 0.8 parts and from about 0.4 to about 0.6 parts by weight. In a particular embodiment, the photo initiator is CQ and is present in the preparative solution at a concentration of about 0.5 parts by weight.

As described above, the curable composite of the invention includes an ethylenically unsaturated functional monomer, a polyethylenically unsaturated functional crosslinking monomer, optionally, a solvent and, optionally, water, all components in an amount to equal a total of 100 parts by weight.

Suitable ethylenically unsaturated functional monomer components of the curable composite include those described above. Suitable ranges for the ethylenically unsaturated functional monomer component of the curable composite include from about 10 to about 30 parts, from about 15 to about 25 parts, and from about 8 to about 22 parts, all by weight. In a particular embodiment, the ethylenically unsaturated functional monomer component of the curable composite is 2-hydroxyethylmethacrylate at a concentration of about 20 parts by weight.

Suitable polyethylenically unsaturated functional crosslinking monomers of the curable composite include those as described above. Suitable ranges for the polyethylenically unsaturated functional crosslinking monomer of the curable composite include from about 50 to about 90 parts, from about 60 to about 80 parts, and from about 3 to about 78 parts, all by weight.

In certain aspects of the invention the polyethylenically unsaturated functional crosslinking component of the curable composite is a combination of two or more crosslinking monomers. For example, in one embodiment, PMGDM and bis-GMA are used in combination. When two or more crosslinking monomers are used in combination, suitable ranges for each component vary to equal the total parts as described above. More specifically, suitable ranges for a first crosslinking agent include from about 60 to about 75 parts, from about 63 to about 75 parts and from about 65 to about 70 parts and suitable ranges for a second crosslinking agent include from about 5 to about 15 parts, from about 8 to about 12 parts and from about 10 to about 15 parts, all by weight. In a particular aspect, the PMGDM of the curable composite is present at a concentration of about 10 parts by weight and the bis-GMA of the preparative solution is present at a concentration of about 66 parts by weight.

Suitable optional solvents for the solvent component of the curable composite include those described above. Suitable ranges for the solvent component of the curable composite include from about 0 to about 15 parts, from about 0 to about 10 parts, and from about 0 to about 5 parts, all by weight. In a particular embodiment, the curative composite is non-aqueous; it contains less than 2 parts by weight of water.

The curable composition generally includes a photoinitiator system. The photoinitiator system includes a light-sensitive initiator and a polymerization accelerator. A suitable light-sensitive initiator is camphorquinone and a suitable polymerization accelerator is ethyl N, N-dimethyl-4-aminobenzoic acid (EDMAB) or N,N-dimethylaminoethyl methacrylate. Suitable ranges for incorporation of an accelerator include from about 0.1 to about 7 parts, 1 to about 5 parts and about 2 to about 3 parts by weight.

Since most of the polymerization reactions which ethylenically unsaturated compounds undergo, particularly acrylate and methacrylate compounds, proceed by a free radical mechanism, a free radical initiator is generally included in the monomer system. Any free radical initiator, which is substantially non-toxic in the amounts employed in the composition; which does not react adversely with either the polymeric matrix, once formed, and cures within a few minutes is acceptable. The free radical initiator may be of the chemical type (redox system) in which a peroxide initiator and a polymerization accelerator react at ambient temperatures to initiate the polymerization of the monomer system. Alternatively, a photoinitiator system is used in which light, such as ultraviolet light, but preferably the visible portion of the spectrum, is employed as the energy source to stimulate the free radical initiator.

Examples of such chemical initiators include hydroperoxides, peresters or peroxides such as benzoyl peroxide, or amines, tertiary aromatic amines, such as N,N-dimethyl toluidine can be used. Suitable photoinitiators include benzil 2,3-butanedione, phenyl-1,2-propandione, and camphorquinone (CQ).

Suitable ranges of a photo initiator for the curable composition include from about 0.1 to about 1 part, from about 0.2 to about 0.8 parts and from about 0.4 to about 0.6 parts by weight. In a particular embodiment, the photo initiator is CQ and is present in the curable composition at a concentration of about 0.5 parts by weight.

Suitable light sources that are effective to cause photoinitiation to occur include halgoen, laser, plasma and LED sources. The amount of energy required, is that amount which is sufficient to initiate a photochemical reaction such that polymerization of the ethylenically unsaturated components is started or enhanced. One skilled in the art can determine the amount of light required to cause such reaction to occur and many light systems are commercially available.

The present invention further provides packaged formulations of the etch solutions and/or gel etchant, the curable compositions, combinations thereof.

For example, the present invention provides a packaged three part dental bonding system that includes three containers. The first container includes an etch solution as described above, comprising an inorganic acid, present in an amount of from about 1 to about 10 parts by weight; an organic acid, present in amount from about 0.1 to about 10 parts by weight; a solvent present in an amount from about 0 to about 65 parts by weight; an ethylenically unsaturated functional monomer, present in an amount from about 0.1 to about 10 parts by weight and water, present in an amount from about 0 to about 50 parts by weight, all components in an amount to equal a total of 100 parts by weight.

The second container includes a preparative solution comprising an ethylenically unsaturated functional monomer, present in an amount of from about 5 to about 25 parts by weight; a polyethylenically unsaturated functional crosslinking monomer, present in an amount of from about 10 to about 40 parts by weight; a solvent present in an amount from about 0 to about 65 parts by weight; and water, present in an amount from about 0 to about 50 parts by weight, all components in an amount to equal a total of 100 parts by weight.

The third container includes a curable composite an ethylenically unsaturated functional monomer, present in an amount of from about 10 to about 30 parts by weight; a polyethylenically unsaturated functional crosslinking monomer, present in an amount of from about 50 to about 90 parts by weight; a solvent present in an amount from about 0 to about 15 parts by weight; and water, present in an amount from about 0 to about 15 parts by weight, all components in an amount to equal a total of 100 parts by weight.

In another embodiment, the present invention provides a packaged three part dental bonding system that includes three containers. A first container includes an etch solution comprising nitric acid, present in an amount of from about 1 to about 10 parts by weight; succinic acid, present in amount from about 0.1 to about 10 parts by weight; methacrylic acid, present in an amount from about 0.1 to about 10 parts by weight and water, present in an amount to equal a total of 100 parts by weight.

A second container includes a preparative solution comprising hydroxymethylacrylate, present in an amount of from about 5 to about 25 parts by weight; PMGDM, present in an amount of from about 15 to about 25 parts by weight; bis-GMA, present in an amount of from about 5 to about 12 parts by weight; ethanol present in an amount from about 25 to about 35 parts by weight; and acetone, present in an amount from about 20 to about 30 parts by weight, all components in an amount to equal a total of 100 parts by weight.

A third container includes curable composite comprising hydroxymethylacrylate, present in an amount of from about 15 to about 25 parts by weight; bis-GMA, present in an amount of from about 60 to about 70 parts by weight; and PMGDM, present in an amount of from about 5 to about 15 parts by weight, all components in an amount to equal a total of 100 parts by weight.

In still another embodiment, the present invention provides a packaged three part dental bonding system that includes three containers. A first container includes an etch solution comprising nitric acid, present in an amount of about 5 parts by weight; succinic acid, present in amount of about 2.5 parts by weight; methacrylic acid, present in an amount of about 2.5 parts by weight and water, present in an amount to equal a total of 100 parts by weight.

A second container includes a preparative solution comprising hydroxymethylacrylate, present in an amount of about 15 parts by weight; PMGDM, present in an amount of about 20 parts by weight; bis-GMA, present in an amount of about 8 parts by weight; ethanol present in an amount of about 30 parts by weight; and acetone, present in an amount of about 26 parts by weight, all components in an amount to equal a total of 100 parts by weight.

A third container includes a curable composite comprising hydroxymethylacrylate, present in an amount of about 20 parts by weight; bis-GMA, present in an amount of about 66.5 parts by weight; and PMGDM, present in an amount of about 10 parts by weight; EDMAB, present in an amount of about 3 parts by weight; CQ, present in an amount of about 0.5 parts by weight, all components in an amount to equal a total of 100 parts by weight.

Instructions are provided for the application of the etch solution to a bone substrate, i.e., a tooth, such that the substrate is conditioned for further treatment with a preparative solution or a curable composite. The instructions provide the length of time the solution is applied, how to remove excess solution, how to then treat the etched surface with a preparative solution and then how to bond a restorative material, e.g. a fixture to the treated substrate with the curable composite. Instructions for these applications are described throughout the specification.

It should be understood that the gel etchants described throughout the specification can be used in place of the etch solution in the above-described packaged products.

The containers that can be used for the packaged products are those that are generally commercially available. Any container suitable for retaining the liquids can be used that does not react with the solution(s). The container can be a reusable bottle, as known in the art, a single use bottle, syringe or pouch. The container can be collapsible, such as those foil packets known in the art. In certain embodiments, it is advantageous to provide a container that does not permit light to penetrate through the bottle. The solutions can be stored at or below room temperature, so that the container should be to withstand temperatures below room temperature. Bottles or packets prepared from polyethylene or polypropylene are suitable as well as those aluminized foil packets prepared from various terephthalates.

The present invention also provides methods to use the etch solutions or gel etchants. It should be understood that the etch solutions or gel etchants and preparative solutions of the present invention can be used with those commercially available bonding resins. The method of the invention involves applying an effective amount of an etching solution or gel etchant to the substrate. The etch solution or gel etchant can be any of the solutions or gels described herein, and for example, can include an inorganic acid, an organic acid, an ethylenically unsaturated functional monomer and water.

Generally, the etch solution or gel is applied by a microbrush, a swab, a syringe, or a sponge. The solution is applied to the treated area, i.e., a cavity, for between about 1 second and about 60 seconds with gentle agitation. Generally, the solution is not removed from the treated surface. Generally the gel is removed prior to additional treatment.

Optionally, the excess etching solution can be removed from the substrate such that the substrate remains moist. This can be easily accomplished by touching an absorbent material to the surface and blotting the excess from the surface or by passing compressed air over the treated surface. Thereafter, a preparative solution is applied to the moist substrate, i.e., a tooth.

Generally, the preparative solution of the invention is applied to the treated surface with a microbrush or the like. This can be accomplished with one or more applications, often times, 3 applications. After the preparative solution is applied and coated onto the substrate surface, it is generally dried for approximately about 1 to about 30 seconds, i.e., about 10 seconds, by air thinning with compressed air. It is recommended that the force of the compressed air is increased over that time period. After air-drying of the treated surface, the treated surface should appear to be dry.

A curable composite is applied to the treated substrate, i.e., a tooth. Generally, the curable composite is dispensed via syringe to effect a thin layer of the curable composite over the pre-treated substrate area. The curable composite is generally air thinned for between about 1 and about 60 seconds, i.e., about 3 to about 5 seconds. The air-thinned surface coated curable composite is then subjected to light activation for a sufficient period of time, i.e., between about 10 and about 60 seconds.

The present invention also provides methods for adhering a material to a substrate, i.e., a dental substrate. The methods generally include applying an effective amount of an etching solution and/or a gel etchant, applying a preparative solution and applying a curable composite to the substrate as described throughout the specification. Thereafter, the curable composite can be exposed to a light source that emits an effective amount of energy to cure the composite. Suitable energy sources include lasers, UV light apparatus, LED type curing lights, or a quartz-tungsten halogen curing mechanisms. A restorative material can be adhered to the composite thereafter.

The phrase "effective amount of an etching solution" or "effective amount of a dental etching solution" is that amount required to modify the surface architecture of the bone substrate. Not to be limited by theory, it is believed that the etching solution removes proteins, lipids, and other foreign materials from the surface of the substrate and penetrates into the substrate. The surface and the penetrated substrate area are cleaned and modified such that they are receptive toward further modification, i.e., a curable composite where reactive functionality such as ethylenic bonds can attach to the modified material. A skilled artisan can readily determine the amount of etch solution to apply to the substrate, however, only enough of the solution is required so as to wet the surface and keep it moist as the surface is modified during rubbing.

The phrases "removing excess etching solution" or "removing excess dental etching solution" is intended to mean that a sufficient amount of the etching solution is removed from the substrate so that the surface remains wetted, i.e., moist. This can be accomplished by a variety of ways, including but not limited to, contacting the wet surface with an absorbent material, i.e., a cotton swab or tissue, passing a stream of air over the surface, and other methods known in the art. Ideally, enough etch solution should remain so that the surface of the substrate remains moist and does not become dry.

In an exemplary method, the substrate material is cleaned with isopropyl alcohol, rinsed with water and dried for at least 3 seconds. 1-2 drops of the etch solution are placed in an open well receptacle and a cotton or foam pellet is contacted to the solution. The moistened applicator is contacted to the substrate such that the area to be treated is wetted. The applicator is gently agitated with the solution against the surface for at least about 1 0 to about 30 seconds, i.e., from about 10 to about 30 seconds, from about 10 to about 20 seconds, or from about 10 to about 15 seconds.

Generally, the etch solution is allowed to remain on the substrate surface for approximately 10 to about 30 seconds, i.e., from about 10 to about 20 seconds, or from about 10 to about 15 seconds. During this time, the applicator is then pressed against an absorbent material, such as a patient napkin or to a facial tissue, to remove most of the liquid from the applicator. The wetted surface is contacted to the partially dried applicator to remove the excess etch solution while leaving the surface visibly moist. Alternatively, the wetted surface can be partially dried by passing compressed air over the treated surface area. Ideally, the preparation should not be allowed to dry. There is no requirement to rinse the etch solution from the surface before any further applications are done.

After treatment with the etch solution, a preparative solution, as described throughout the specification, is applied to the etch treated surface as described above.

After the preparative treatment is complete, from about 1 to about 3 coats of an adhesive resin, such as those that are available commercially or those described within the present application, can be applied directly over the moist conditioned preparation with a suitable applicator, such as a brush. The adhesive resin is dried gently, for about 5-8 seconds to facilitate evaporation of the solvent. After the surface is dried, the surface should appear to be "shiny," if not, additional resin adhesive should be applied. The adhesive resin is then light-cured for about 10 seconds. Optionally, a restorative material can be applied to the adhesively treated surface to continue the procedure. However, depending upon what therapeutic treatment is intended, the adhesive resin can serve as a protectant covering and no further restorative treatment may be necessary.

For example, the three-part system can be used to seal enamel/dentin prior to restoration with light-cured or self-cured composite materials. Indirect Restorations are also encompassed by the present invention and include those preparations when using a light-cured, self-cured or dual-cured composite cement or glass ionomer or resin-modified glass ionomer cement. The methods and compositions of the invention can also be useful for desensitization to treat hypersensitive and/or exposed root surfaces. Additionally, the methods and compositions of the invention can be used to bond in a post and core.

The phrases "effective amount of a gel etching composition", "effective amount of a gel etchant" or "effective amount of a dental gel etching composition" is that amount required to modify the surface architecture of the bone substrate. Not to be limited by theory, it is believed that the etching gel removes proteins, lipids, and other foreign materials from the surface of the substrate and penetrates into the substrate. The surface and the penetrated substrate area are cleaned and modified such that they are receptive toward further modification, i.e., a curable composite where reactive functionality such as ethylenic bonds can attach to the modified material. A skilled artisan can readily determine the amount of etching gel to apply to the substrate, however, only enough of the gel is required so as to wet the surface and keep it moist as the surface is modified during application.

The phrases "removing excess gel etching composition" or "removing excess dental gel etching composition" is intended to mean that a sufficient amount of the gel etching solution is removed from the substrate so that the surface remains wetted, i.e., moist. This can be accomplished by a variety of ways, including but not limited to, rising the treated surface with water or contacting the gelled surface with an absorbent material, i.e., a cotton swab or tissue, passing a stream of air over the surface, and other methods known in the art.

In an exemplary method, the substrate material is cleaned with isopropyl alcohol, rinsed with water and dried for a few seconds. The gel composition is applied to the treated surface via a syringe. Alternatively, 1-2 drops of the gel composition are placed in an open well receptacle and a cotton or foam pellet is contacted to the gel. The moistened applicator is contacted to the substrate such that the area to be treated is coated with gel. The applicator is gently agitated with the gel against the surface for at least about 10 to about 30 seconds, i.e., from about 10 to about 30 seconds, from about 10 to about 20 seconds, or from about 10 to about 15 seconds.

Generally, the gel etch composition is allowed to remain on the substrate surface for approximately 10 to about 30 seconds, i.e., from about 10 to about 20 seconds, or from about 10 to about 15 seconds.

After treatment with the etch solution, a preparative solution, as described throughout the specification, is applied to the etch treated surface as described above.

After the preparative treatment is complete, from about 1 to about 3 coats of an adhesive resin, such as those that are available commercially or those described within the present application, can be applied directly over the moist conditioned preparation with a suitable applicator, such as a brush. The adhesive resin is dried gently, for about 5-8 seconds to facilitate evaporation of the solvent. After the surface is dried, the surface should appear to be "shiny," if not, additional resin adhesive should be applied. The adhesive resin is then light-cured for about 10 seconds. Optionally, a restorative material can be applied to the adhesively treated surface to continue the procedure. However, depending upon what therapeutic treatment is intended, the adhesive resin can serve as a protectant covering and no further restorative treatment may be necessary.

For example, the etching/adhesive system can be used to seal enamel/dentin prior to restoration with light-cured or self-cured composite materials. Indirect Restorations are also encompassed by the present invention and include those preparations when using a light-cured, self-cured or dual-cured composite cement or glass ionomer or resin-modified glass ionomer cement. The methods and compositions of the invention can also be useful for desensitization to treat hypersensitive and/or exposed root surfaces. Additionally, the methods and compositions of the invention can be used to bond in a post and core.

Restorative materials applicable for use with the present invention include those known in the art. Composite materials, synthetic bone materials, bone-like apatite and hydroxyapatite materials are well suited for use with the compositions and methods of the invention. Suitable examples of dental restoratives include composite filling materials, inlays, onlays, crown, bridges, ceramics, veneers and Maryland bridges.

The invention is further illustrated by the following examples, which in no way should be construed as being further limiting. The contents of all references, pending patent applications and published patent applications, cited throughout this application, including those referenced in the background section, are hereby incorporated by reference. It should be understood that the models used throughout the examples are accepted models and that the demonstration of efficacy in these models is predictive of efficacy in humans.

All samples throughout the experiments were prepared prior to testing. The test sample was steam sterilized for 24 hours prior to treatment. The preparation included that a tooth was stabilized and embedded into a cylindrical mounting with a polymerizable monomer, such as methyl methacrylate. The tooth surface was ground until 4 mm of appropriate surface was exposed, i.e., enamel or dentin. The surface was finely polished, rinsed, dried and then treated.

Samples denoted as "No rinse" were treated with a solution of 5% by weight nitric acid, 2.5% by weight succinic acid and 2.5% by weight methacrylic acid (with the balance being water to equal 100 parts by weight) for approximately 15 seconds.

Without an intervening rinse step, the surface was then subjected to a preparative solution by dabbing the surface with three brushfuls of a solution comprising 15% by weight hydroxymethylacrylate, 25% by weight PMGDM, acetone, ethanol, 0.5% by weight camphoroquinone (CQ) and 1.0% Darocur (to equal 100 parts by weight) followed by drying for about 10 seconds.

Without an intervening rinse step, the dried surface was then coated several times with the adhesive resin of 61% by weight bis-GMA, 27% by weight HEMA, 3% by weight PMDM, 5% by weight TEGDMA, 3% by weight ethyldimethylaminobenzoic acid (EDMAB) and 0.5% by weight camphoroquinone (CQ) (to equal 100 parts by weight).

The coated resin was subjected to light activation for 10 seconds with a Demetron 401 light generating unit (Demetron-Kerr) and then a piece of Z100 composite (Minnesota Manufacturing & Mining, St. Paul, Minn.) was adhered to the treated surface followed by light activation for an additional 40 seconds. Testing was performed on the resulting composite after the period of time noted below.

Samples denoted as "Rinse Etchant" were treated with APEX GEL ETCHANT™, composed of 9% by weight gelling agent, Aerosil 200, 5% by weight nitric acid, 2.5% by weight succinic acid and 2.5% by weight methacrylic acid, with the balance being water (to equal 100 parts by weight) for approximately 15 seconds. The treated surface was rinsed with and air-water spray for 5 seconds prior to treatment with a preparative solution. The excess water was blotted from the surface with a cotton pellet or foam sponge, leaving the surface moist.

The rinsed surface was then subjected 3 coats of a preparative solution comprising of a solution comprising 15% by weight hydroxymethylacrylate, 25% by weight PMGDM, acetone, ethanol, 1.0% Darocur and 0.5% by weight camphoroquinone (CQ) (to equal 100 parts by weight) and then dried for about 10 seconds.

The dried surface was then coated three times with an adhesive resin 61% by weight bis-GMA, 27% by weight HEMA, 3% by weight PMDM, 5% by weight TEGDMA, 3% by weight ethyldimethylaminobenzoic acid (EDMAB) and 0.5% by weight camphoroquinone (CQ) (to equal 100 parts by weight).

The coated resin was subjected to light activation for 10 seconds with a Demetron 401 light generating unit (Demetron-Kerr) and then a piece of Z100 composite (Minnesota Manufacturing & Mining, St. Paul, Minn.) was adhered to the treated surface followed by light activation for an additional 40 seconds. Testing was performed on the resulting composite after the time noted below.

The samples were stored in water at 37° C. for a given period of time. For testing purposes, the samples were subjected to shear bond strength testing on a Universal testing machine with a crosshead speed of 1 mm/min. The force required to break the composite from the surfaces was recorded in kg and converted to mPa on the basis of the surface area of the sample. The results are provided in the following table:

| Time | Surface | No Rinse | Rinse Etchant |
| --- | --- | --- | --- |
| Immediate | Dentin | 33-36 mPa | 34-36 mPa |
| Immediate | Enamel | 25-28 mPa | 32-34 mPa |
| 24 hours | Dentin | 53-55 mPa | 53-56 mPa |
| 24 hours | Enamel | 40-44 mPa | 44-46 mPa |
| 6 month | Dentin | 53 mPa | 54-57 mPa |
| 6 month | Enamel | 44 mPa | 44-46 mPa |

For comparison purposes, tests were performed with OPTIBOND FL® (Kerr Corporation, Orange, California) and Z-100 as described above. This resin bonding system that has been commercially available for more than a decade. Dentin samples had immediate bond strengths of 32 mPa and 24 hour bond strength of 43 mPa. The samples were prepared using the manufacturer's standard method. These results demonstrate that the present invention is equivalent to or better than existing technology.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

I claim

1. A method for adhering a material to a dental substrate, comprising the steps of:
  (a) applying to a dental substrate an effective amount of a dental etching solution, said etch solution comprising an inorganic acid, present in an amount of from about 1 to about 10 parts by weight; an organic acid, present in amount from about 0.1 to about 10 parts by weight; a solvent present in an amount from 0 to about 65 parts by weight; an ethylenically unsaturated functional monomer, present in an amount from about 0.1 to about 10 parts by weight and water, present in an amount from 0 to about 50 parts by weight, all components in an amount to equal a total of 100 parts by weight;
  (b) applying a second preparative solution to the dental substrate treated in step (a), said preparative solution comprising an ethylenically unsaturated functional monomer, present in an amount of from about 5 to about 25 parts by weight; a polyethylenically unsaturated functional crosslinking monomer, present in an amount of from about 10 to about 40 parts by weight; a solvent present in an amount from 0 to about 65 parts by weight; and water, present in an amount from 0 to about 50 parts by weight, all components in an amount to equal a total of 100 parts by weight;
  (c) applying a curable composite to the dental substrate treated in step (b), said curable composite comprising an ethylenically unsaturated functional monomer, present in an amount of from about 10 to about 30 parts by weight; a polyethylenically unsaturated functional crosslinking monomer, present in an amount of from about 50 to about 90 parts by weight; a solvent present in an amount from 0 to about 15 parts by weight; and water, present in an amount from 0 to about 15 parts by weight, all components in an amount to equal a total of 100 parts by weight; and
  (d) exposing the treated dental surface to a light source that emits an effective amount of energy to cure the composite.

2. The method of claim 1, wherein the inorganic acid of step (a) is selected from the group consisting of nitric acid, sulfuric acid, hydrochloric acid and phosphoric acid.

3. The method of claim 1, wherein the inorganic acid of step (a) is nitric acid.

4. The method of claim 1, wherein the organic acid of step (a) is selected from the group consisting of lactic acid, pyruvic acid, glycolic acid, chioroacetic acid, dichioroacetic acid, trichioroacetic acid, cyanoacetic acid, tartaric acid, succinic acid, glutaric acid, maleic acid, fumaric acid, malonic acid, citraconic acid, ortho-phthalic acid, meta-phthalic acid, para-phthalic acid, citric acid, tricarballyic acid, 1,3,5-pentanetricarboxylic acid and trimellitic acid.

5. The method of claim 1, wherein the organic acid of step (a) is succinic acid.

6. The method of claim 1, wherein the ethylenically unsaturated functional monomer of step (a) is methacrylic acid.

7. The method of claim 1, wherein the ethylenically unsaturated functional monomer or step (b) is hydroxyethylmethacrylate.

8. The method of claim 1, wherein the polyethylenically unsaturated functional crosslinking agent of step (b) comprises two polyethylenically unsaturated functional crosslinking agents.

9. The method of claim 8, wherein the polyethylenically unsaturated functional crosslinking agents are: the reaction product of pyromellitic dianhydride with glycerol dimethacrylate (PMGDM); and 2,2'-bis[4-(3-methacryloxy-2-hydroxy propoxy)-phenyl]-propane (bis-GMA).

10. The method of claim 1, wherein step (b) further comprises a photo initiator.

11. The method of claim 10, wherein the photo initiator is camphorguinone (CQ).

12. The method of claim 1, wherein the ethylenically unsaturated functional monomer of step (c) is hydroxymethylacrylate.

13. The method of claim 1, wherein the polyethylenically unsaturated functional crosslinking monomer of step (c) comprises two polyethylenically unsaturated functional crosslinking agents.

14. The method of claim 13, wherein the polyethylenically unsaturated functional crosslinking agents are: the reaction product of pyromellitic dianhydride with glycerol dimethacrylate (PMGDM); and 2,2'-bis[4-(3-methacryloxy-2-hydroxy propoxy)-phenyl]-propane (bis-GMA).

15. The method of claim 1, wherein step (c) further comprises a photo initiator system.

16. The method of claim 15, wherein the photo initiator system comprises a light-sensitive initiator and a polymerization accelerator.

17. The method of claim 16, wherein the light sensitive initiator is camphorquinone (CQ) and the polymerization accelerator is ethyl N,N-dimethyl-4-aminobenzoic acid (EDMAB).

* * * * *